United States Patent [19]
Lin et al.

[11] Patent Number: 6,136,030
[45] Date of Patent: Oct. 24, 2000

[54] PROCESS FOR PREPARING POROUS BIOCERAMIC MATERIALS

[75] Inventors: Feng-Huei Lin; Chun-Jen Liao, both of Taipei, Taiwan

[73] Assignee: Purzer Pharmaceutical Co., Ltd., Taipei, Taiwan

[21] Appl. No.: 09/228,933

[22] Filed: Jan. 12, 1999

[51] Int. Cl.$^7$ .............................. A61F 2/28; A61F 2/44; A61F 2/00; A01N 43/40
[52] U.S. Cl. .............................. 623/16; 623/17; 523/113; 514/324
[58] Field of Search ........................ 623/16, 17; 523/113

[56] References Cited

U.S. PATENT DOCUMENTS

| | | | |
|---|---|---|---|
| 5,571,190 | 11/1996 | Ulrich et al. | 623/17 |
| 5,702,449 | 12/1997 | McKay | 623/17 |
| 5,728,159 | 3/1998 | Stroever et al. | 623/16 |
| 5,977,204 | 11/1999 | Boyan et al. | 523/113 |
| 5,985,897 | 11/1999 | Muehl et al. | 514/324 |

FOREIGN PATENT DOCUMENTS

| | | |
|---|---|---|
| 88/03417 | 5/1988 | WIPO . |
| 98/16267 | 4/1998 | WIPO . |

OTHER PUBLICATIONS

D.C. Tancred, B.A.O McCormack, A.J. Carr, "A synthetic bone implant macroscopically identical to cancellous bone", Biomaterials 19 (1999) 2303–2311.

Feng–Huei Lin, Chun–Jen Liao, Ko–Shao Chen, Jui–Sheng Sun, "Preparation of a biphasic porous bioceramic by heating bovine cancellous bone with Na4P207–10H20 addition", Biomaterials 20 (1999) 475–484.

D.C. Tancred, A.J. Carr, B.A.O McMormack, "Development od a new synthetic bone graft", Journal of Materials Science: Materials in Medicine 9 (1998) 819–823.

*Primary Examiner*—Michael J. Milano
*Assistant Examiner*—Hieu Phan
*Attorney, Agent, or Firm*—Bacon & Thomas, PLLC

[57] ABSTRACT

A process for preparing porous bioceramic materials includes the following steps: (a) using the cancellous bone of animals, (b) removing organic substances in the cancellous bone by thermal processing to obtain de-organic cancellous bone, (c) soaking the de-organic cancellous bone in a solution of phosphate salts, and (d) obtaining porous bioceramic materials by sintering up to 900° C. or higher after dehydration. The porous bioceramic materials of the present invention are suitable for use as filling materials for bone defect.

12 Claims, 2 Drawing Sheets

PROCESS FOR PREPARING POROUS BIOCERAMIC MATERIALS

FIELD OF THE INVENTION

The present invention relates to a process for preparing porous bioceramic materials.

BACKGROUND OF THE INVENTION

The most important problem nowadays for hetero-bone implant is immunological defensive reaction occurring in the biological body. Previously many researchers dealt with this by different methods, such as freezing, boiling or chemical soaking, but the immuno-defensive reaction, evoked by the hetero-bone implant, could not be avoided by these methods. In 1988, Mittelmeier et al. used high-temperature heating to sinter bovine bone in order to remove all the organic components that might cause immuno-defensive reaction, whereas the biocompatible inorganic components remained. Because the major inorganic substance in bone is $Ca_{10}(PO_4)_6(OH)_2$ (hydroxyapatite; HAP), after the removal of organic components the remnant mineral is like a crystalline mold of metallurgic powder. In the continuous heating process of the remnant mineral, a strong ceramic sinter can be obtained. Because bovine bone is cancellous, it has a natural porous structure, and the porosity can be as high as 70 vol %. Therefore, a natural porous bioceramic material, mainly composed of HAP, can be obtained by using this method. At the present time this material has been widely used in clinical bone surgery as a bone defect filling material.

The major inorganic component in raw cancellous bone is HAP, which is the same as in human bone. Consequently, it has a good biocompatibility. However, also due to the similar compositions, which reduce the bioactivity. In recent years, some researchers added highly soluable $\beta$-tricalcium phosphate $(Ca_3(PO_4)_2; \beta$-TCP$)$ in HAP to form a biphasic (HAP/$\beta$-TCP) bioceramic material. In animal experiments, implant of biphasic bioceramic material in bone tissue demonstrated a better clinical effect than pure HAP or pure $\beta$-TCP.

SUMMARY OF THE INVENTION

The object of the present invention is to provide a process for preparing porous bioceramic materials; this process can produce excellent bone implant substitutes.

It is another object of the present invention to provide a process for preparing porous bioceramic materials, in which porous bioceramic materials of various crystalline compositions can be obtained.

It is still another object of the present invention to provide a process for preparing porous bioceramic materials, in which the crystalline compositions ratios of obtained porous bioceramic materials cain be controlled.

The present invention provides a process for preparing a porous bioceramic material. Generally the process includes (a) using a cancellous bone of animal, (b) removing organic substances in the cancellous bone by thermal processing to obtain a de-organic cancellous bone, (c) soaking the de-organic cancellous b)one in a solution of phosphate salts, and (d) obtaining porous bioceramic material by sintering up to 900° C. or higher. Thus porous bioceramic material of various crystalline compositions can be obtained.

By using the manufacturing process of the present invention, porous bioceramic materials containing HAP/$\beta$-TCP biphasic or HAP/$\beta$-TCP/SCP triphasic structures can be obtained. Even porous bioceramic materials containing $\beta$-TCP/SCP biphasic or $\beta$-TCP single physic structures can be obtained. SCP here is sodium calcium phosphate ($NaCaPO_4$).

Porous bioceramic materials of HAP/$\beta$-TCP biphasic or HAP/$\beta$-TCP/SCP triphasic structures are multiphasic porous bioceramic materials containing HAP. Implant of these biphasic bioceramic material in bone tissue has demonstrated a better clinical effect than pure HAP or pure $\beta$-TCP.

Furthermore, by using the manufacturing process of the present invention and adding solutions of phosphate salts at various concentrations, bioceramics of different biphasic structures, due to different HAP/$\beta$-TCP composition ratios, can be obtained.

DETAILED DESCRIPTION OF THE PREFERRED EMBODIMENT

Figure 1:
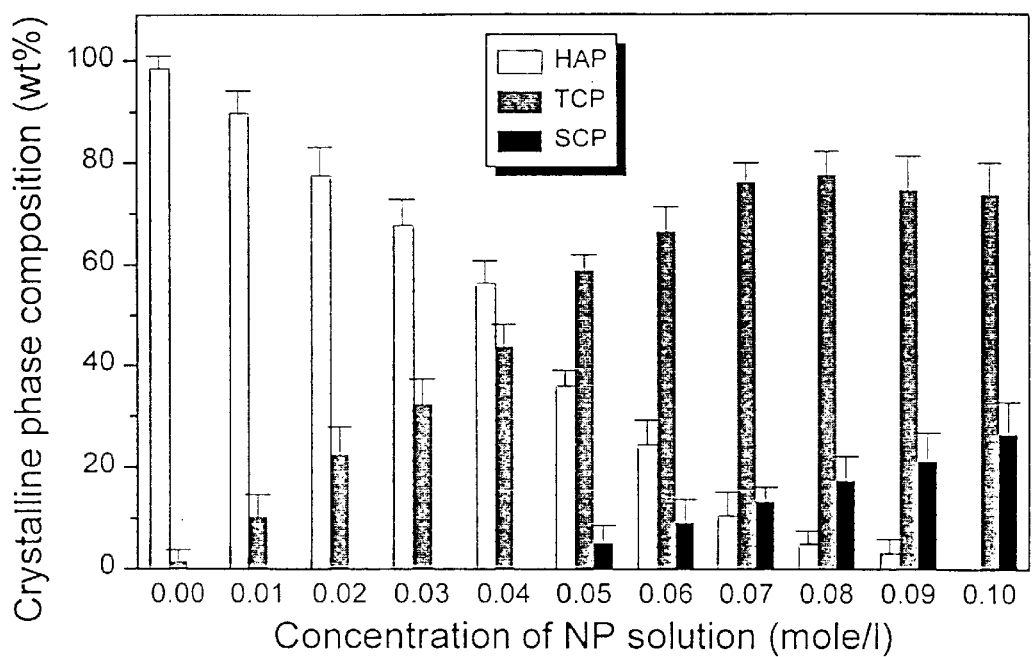
FIG. 1 shows the relationships between soaking concentration of sodium pyrophosphate solution and the obtained porous bioceramic materials from bovine cancellous bone, in example 1 to 10.

In the present invention, the preparing process to produce porous bioceramic materials is using the cancellous bone of animals, removing organic substances in the cancellous bone by thermal processing to obtain a de-organic cancellous bone, soaking the de-organic cancellous bone in a solution of phosphate salts, and obtaining biphasic porous bioceramic materials by sintering up to 900° C. or higher after dehydration.

In the manufacturing process of the present invention, the cancellous bone of animals can be from any animal; there is no special limitation. Generally the cancellous bone from mammals are the most suitable. It could be bovine, horse, hog, rabbit, rat, chicken, duck, goose, or fish. There is also no limitation in size and shape. Generally speaking, the hog or bovine cancellous bone needs to be cut into 0.1–1.0 centimeter cubes.

Cancellous bone of animals is used as the processing material in the manufacturing procedures of the present invention. To prevent excessive cracking inside the material caused by frying in the heating process, the organic substances in cancellous bone of animals need to be removed. There are many well-known methods to remove organic substances from animal bone; in the present invention there is no limitation as long as the organic substances can be removed. The method used in the examples of the present invention was to cook the bovine cancellous bone in boiling water for 6 hours to remove lipid and fat. Then the cancellous bone was dehydrated in alcohol series and dried in an oven at 70° C. for 3 days. After the treatments, the bovine cancellous bone was then put into a platinum crucible located in a high-temperature oven. The thermal processing, removing organic substances by heating, had a heating rate of 5° C./min, and the temperature was kept at 800° C. for 6 hours to ensure that organic substances in the bovine cancellous bone were completely removed.

The solution of phosphate salts used in the present invention could be solutions of alkali metal phosphate, alkaline earth metal phosphate, or phosphate salts such as ammonium phosphate (($NH_4)_2HPO_4$).

After the removal of organic substances, cancellous bone of animals was soaked in solutions of phosphate salts at various concentrations. Then various porous bioceramic materials can be obtained by sintering up to 900° C. or higher after dehydration.

For crystalline structure determination of obtained porous bioceramic materials, X-ray diffractometer (XRD), Fourier-transformed infrared (FTIR) and scanning electron microscope (SEM) can be used to determine both the component and ratio. These techniques are not stated here since they are well known.

More detailed examples are used to illustrate the present invention, and these examples are used to explain the present invention. The examples below, which are given simply by way of illustration, mist not be taken to limit the scope of the invention.

EXAMPLE 1

Cancellous bone was obtained from calf femoral condyles, cut into small cube of approximately 1.0 cm$^3$. The raw bone was cooked in boiling water for 6 hours to remove lipid and fat. Then the cancellous bone was dehydrated in alcohol series and dried in an oven at 70° C. for 3 days. After the treatments, the bovine cancellous bone was then put into a platinum crucible located in a high-temperature oven. The thermal processing, removing organic substances by heating, had a heating rate of 5° C./min, The temperature was kept at 800° C. for 6 hours to ensure that organic substances in the bovine cancellous bone were completely removed.

The bovine cancellous bone, without organic substances, was soaked in 0.01 mole/liter sodium pyrophosphate solution for 24 hours. Then the bone was taken out and excess solution was removed by filter paper, and the bone was dehydrated in an oven at 70° C.

After dehydration, the bovine bone was sintered up to 1300° C., and HAP/β-TCP biphasic porous bioceramic materials were obtained. The relationship between the concentration of sodium pyrophosphate soaking solution and the obtained porous bioceramic material is shown in FIG. 1.

EXAMPLES 2 to 4

The procedure was similar to example 1, but the concentrations of sodium pyrophosphate solutions were 0.02, 0.03, and 0.04 mole/liter, respectively. After soaking in sodium pyrophosphate solutionand dehydrating, the bovine bone was sintered up to 1300° C., and HAP/β-TCP biphasic porous bioceramic materials were obtained. The relationships between the concentration of sodium pyrophosphate soaking solution and the obtained porous bioceramic materials are shown in FIG. 1.

EXAMPLES 5 to 9

The procedure was similar to example 1, but the concentrations of sodium pyrophosphate solutions were 0.05, 0.06, 0.07, 0.08, and 0.09 mole/liter, respectively. After soaking in sodium pyrophosphate solution and dehydrating, the bovine bone was sintered up to 1300° C., and HAP/β-TCP/SCP triphasic porous bioceramic materials were obtained. The relationships between the concentration of sodium pyrophosphate soaking solution and the obtained porous bioceramic materials are shown in FIG. 1.

EXAMPLE 10

The procedure was similar to example 1, but the concentration of sodium pyrophosphate solution was 0.10 mole/liter. After soaking in sodium pyrophosphate solution and dehydrating, the bovine bone was sintered up to 1300° C., and β-TCP/SCP biphasic porous bioceramic materials were obtained. The relationship between the concentration of sodium pyrophosphate soaking solution and the obtained porous bioceramic material is shown in FIG. 1.

EXAMPLES 11 to 19

The procedure was similar to example 1, but 0.05, 0.1, 0.2, 0.3, 0.4, 0.5, 0.6, 0.7, and 0.8 mole/liter, respectively, of ammonium phosphate solutions were used for soaking. After soaking in ammonium phosphate solution, the bovine bone was sintered tip to 1300° C., and HAP/β-TCP biphasic porous bioceramic materials could be obtained. The relationship between soaking concentration of ammonium phosphate solution and the obtained porous bioceramic materials are shown in FIG. 2.

EXAMPLES 20 to 21

The procedure was similar to the example 1, but the concentrations of ammonium phosphate solutions were 0.9 and 1.0 mole/liter, respectively. After soaked in ammonium phosphate solution and dehydrating, the bovine bone was sintered up to 1300° C., and β-TCP singles phasic porous bioceramic materials were obtained. The relationship between the concentration of ammonium phosphate soaking solution and the obtained porous bioceramic materials are shown in FIG. 2.

Figure 2:
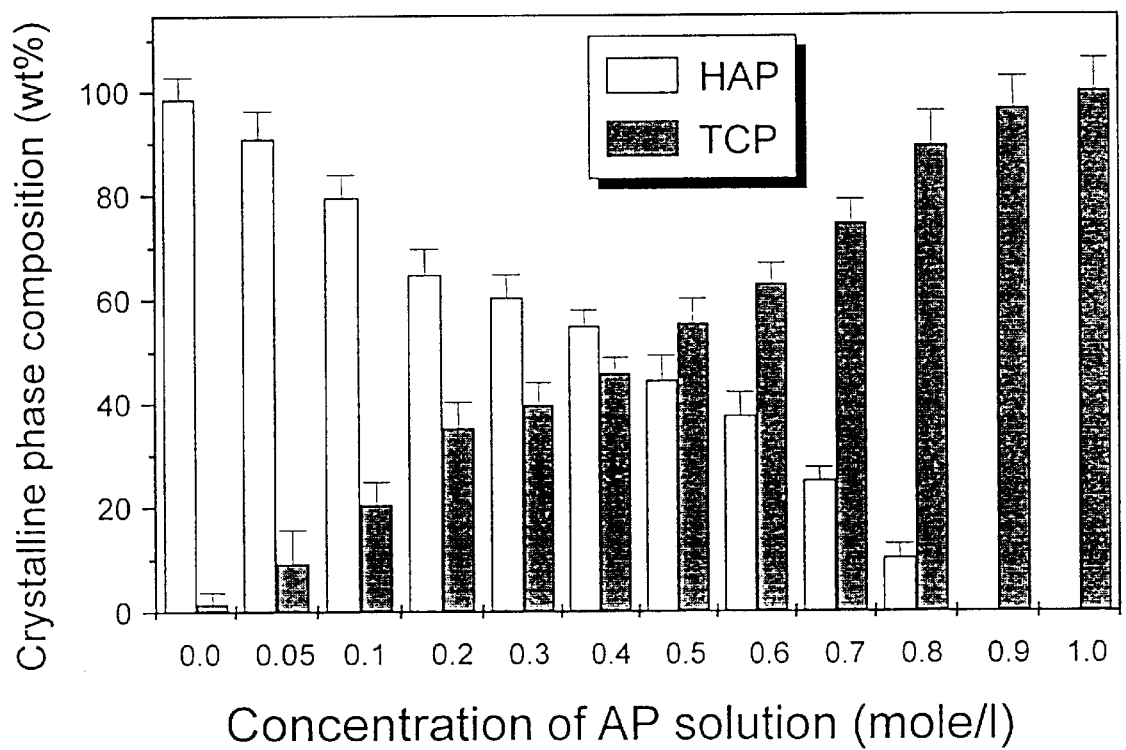
FIG. 2 shows the relationships between soaking concentration of sodium pyrophosphate solution and the obtained porous bioceramic materials from bovine cancellous bone, in example 10 to 20.

From FIGS. 1 and 2, it is obvious that the manufacturing procedure of the present invention can not only produce various porous bioceramic materials, but also control the crystalline structure and component ratio of the obtained porous bioceramic materials by using different kinds of phosphate salts and solution concentrations.

From the foregoing description, ore skilled in the art can easily ascertain the essential characteristics of this invention, and, without departing from the scope thereof, can make various changes and modifications of the invention to adapt it to various usages and conditions. Thus, other embodiments are also within the claims.

What is claimed is:

1. A process for preparing a porous bioceramic material comprising the steps of:
   (a) using a cancellous bone of animal;
   (b) removing organic substances in the cancellous bone by thermal processing to obtain a de-organic cancellous bone;
   (c) soaking the de-organic cancellous bone in a solution of phosphate salts; and
   (d) obtaining a porous bioceramic materials by sintering up to 900° C. or higher.

2. The process of claim 1, wherein the animal cancellous bone is a bovine cancellous bone.

3. The process of claim 1, wherein the thermal processing in step (b) is to cook the bovine cancellous bone in boiling water to remove lipid and fat, take out the bovine cancellous bone for dehydration, and heat the bovine cancellous bone between 600° C. and 800° C. to remove organic substances.

4. The process of claim 1, wherein the solution of phosphate salt is a solution of alkali metal phosphate, alkaline earth metal phosphate, or ammonium phosphate ($(NH_4)_2HPO_4$).

5. The process of claim 4, wherein the solution of phosphate salt is a solution of sodium pyrophosphate ($Na_4P_2O_7$, NP).

6. The process of claim 1, wherein the solution of phosphate salt is a solution of sodium pyrophosphate, and the concentration is between 0.001–0.10 mole/liter.

7. The process of claim 1, wherein the porous bioceramic material is HAP/β-TCP biphasic porous bioceramic material.

8. The process of claim 1, wherein the porous bioceramic material is HAP/β-TCP/SCP triphasic porous bioceramic material.

9. The process of claim 1, wherein the cancellous bone in step (a) is to be cut into 0.1–1.0 centimeter cubes.

10. The process of claim 1, wherein the concentration of the solution of sodium pyrophosphate in step (c) is between 0.001–0.09 mole/liter, while the temperature of the high-temperature sintering in step (d) is between 900–1350° C. to obtain HAP/β-TCP biphasic porous bioceramic material or HAP/β-TCP/SCP triphasic porous bioceramic material.

11. The process of claim 1, wherein the solution of phosphate salt is a solution of ammonium phosphate.

12. The process of claim 11, wherein the solution of phosphate salt in step (c) is ammonium phosphate, and the concentration is between 0.001–0.9 mole/liter, while the temperature of the high-temperature sintering in step (d) is between 900–1350° C. to obtain HAP/β-TCP biphasic porous bioceramic material.

* * * * *